United States Patent
Elbrecht et al.

(10) Patent No.: US 6,461,349 B1
(45) Date of Patent: Oct. 8, 2002

(54) MEDICAL HANDPIECE WITH A LIGHT GUIDE WHICH CAN BE DISPLACED IN AN AXIAL DIRECTION

(75) Inventors: Jens Elbrecht; Berlind Kalve; Thomas Kloss, all of Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 09/530,094

(22) PCT Filed: Oct. 23, 1998

(86) PCT No.: PCT/EP98/06736

§ 371 (c)(1),
(2), (4) Date: Apr. 24, 2000

(87) PCT Pub. No.: WO99/21493

PCT Pub. Date: May 6, 1999

(30) Foreign Application Priority Data

Oct. 27, 1997 (DE) .......................................... 197 47 046

(51) Int. Cl.⁷ ............................................... A61B 18/18
(52) U.S. Cl. .............................. 606/16; 606/13; 385/15; 385/25; 385/53
(58) Field of Search ............................... 606/10, 13–16, 606/22, 127, 128, 131; 604/20–22; 385/15, 25, 27, 53, 31

(56) References Cited

U.S. PATENT DOCUMENTS

| | | | | |
|---|---|---|---|---|
| 4,519,390 A | * | 5/1985 | Horne ...................... 128/303.1 |
| 4,526,170 A | * | 7/1985 | Tanner ..................... 128/303.1 |
| 4,694,828 A | | 9/1987 | Eichenbaum |
| 4,785,805 A | | 11/1988 | Joffe et al. |
| 5,011,483 A | * | 4/1991 | Sleister ......................... 606/37 |
| 5,304,172 A | * | 4/1994 | Manoukian et al. .......... 606/15 |
| 5,324,254 A | * | 6/1994 | Phillips ........................ 604/21 |
| 5,364,391 A | * | 11/1994 | Konwitz ....................... 606/16 |
| 5,395,362 A | * | 3/1995 | Sacharoff et al. ............. 606/17 |
| 5,709,689 A | * | 1/1998 | Adams et al. .............. 606/180 |
| 5,735,792 A | * | 4/1998 | Vanden Hoek et al. ...... 600/138 |
| 5,825,958 A | | 10/1998 | Gollihar et al. |
| 5,871,493 A | * | 2/1999 | Sjostrom et al. ............ 606/180 |
| 5,951,544 A | * | 9/1999 | Konwitz ....................... 606/16 |
| 5,957,914 A | | 9/1999 | Cook et al. |
| 5,972,012 A | * | 10/1999 | Ream et al. ................. 606/170 |
| 6,312,402 B1 | * | 11/2001 | Hansmann ................... 604/22 |

FOREIGN PATENT DOCUMENTS

| | | |
|---|---|---|
| DE | 37 39 965 | 9/1988 |
| DE | 41 26 886 | 2/1993 |
| DE | 41 30 591 | 10/1994 |
| EP | 0 507 991 | 10/1992 |

* cited by examiner

Primary Examiner—Linda C. M. Dvorak
Assistant Examiner—A. Farah
(74) Attorney, Agent, or Firm—Reed Smith LLP

(57) ABSTRACT

A medical handpiece for transmitting energy from a laser beam into biological tissue. An optical fiber for conveying the laser beam to the handpiece and a light guide for radiating the laser energy into the tissue are arranged in a base body. Means are provided for aligning the optical axis of the light guide in relation to the optical axis of the fiber and means for aligning the optical axis of the light guide in relation to the base body are also provided. The light guide can be displaced in an axial direction in relation to the base body and the alignment can be set according to the direction of displacement or maintained. The light guide is easy to replace and the device is easy to clean in accordance with all hygiene requirements.

15 Claims, 1 Drawing Sheet

MEDICAL HANDPIECE WITH A LIGHT GUIDE WHICH CAN BE DISPLACED IN AN AXIAL DIRECTION

BACKGROUND OF THE INVENTION a) Field of the Invention

The invention relates to a medical handpiece for transmitting energy from a laser beam into biological tissue in which an optical fiber for conveying the laser radiation and a light guide for radiating the laser energy into the tissue are arranged in a base body.

b) Description of the Related Art

Known handpieces of the type mentioned above have a fixed connection between the light guide and the base body of the handpiece. In this regard, it has been shown that the light guides, which are generally made of quartz or sapphire, wear out after about four operations. The reason for this is that the polished fiber end which comes into contact with the tissue becomes coarsened and is no longer effective for removal. This happens especially with high laser pulse trains and probably results from the formation of cavitation bubbles.

It is disadvantageous that the light guides cannot be exchanged. Accordingly, the entire applicator must be exchanged when the light guide is worn. Because of the permanent connection, not only is the light guide forfeited at the end of the possible period of use, but also the base body and other essential functioning parts of the handpiece are wasted.

A further disadvantage is that the handpiece is difficult to clean because of the very narrow intermediate spaces between the structural component parts in the assembled state. Thus, the space between the cannulae (diameter less than 1 mm) and the light guide (diameter greater than 0.4 mm) must be cleaned completely hygienically; for this purpose, it would be desirable to have a handpiece which could be disassembled, but this would require excellent adjustability of essential functional parts.

U.S. Pat. No. 4,785, 805 describes a device for coupling a laser beam coming from its source into a light guide, wherein a collecting lens is arranged in front of the light guide. This device refers to technical means for achieving a centering of the optical axes of the collecting lens and light guide relative to one another as a precondition for coupling in with the least possible losses. However, in this case there is no need, nor are any technical means provided for this purpose, to align the optical axes of the collecting lens and light guide relative to a suction cannula within which the light guide is to extend in a definite position as is the case in a handpiece of the type mentioned above.

To this extent, this device does not satisfy the requirements for use in such a medical handpiece because this medical handpiece requires that the light guide can be removed when worn and that it can be exactly replaced by a new light guide and aligned in a simple manner with the optical axis of the fiber and suction cannula. Also, a handpiece frequently requires disassembly for purposes of cleaning and, for reasons of time and cost, also requires a subsequent simple realignment of the optical axes and suction cannula. This requirement is not met in the device in the above-cited publication.

An adapter for light guide input coupling for a laser device is described in EP 0 507 991. The adapter contains a sleeve-shaped fitting part for receiving the proximal end of the light guide and is constructed in such a way that blocking and coupling mean are provided in the region of the connection point between the fitting part and a handle, these means enabling the connection of the fitting part and handle only when the light guide is inserted. A light guide for radiating laser energy into biological tissue, for example, which light guide is subject to wear and must therefore be changed frequently and aligned with another light guide and also with a suction cannula in which it extends whenever it is changed, is not provided herein. Consequently, the means disclosed in this reference are not suited to an adequate solution of the above-indicated problems relating to a handpiece.

This relates in an analogous manner to the rinsing catheter according to DE 41 26 886 A1. This rinsing catheter is used to eliminate solids from bodily organs and vessels in humans and animals and is provided with at least two lumens, one of which serves to supply a rinsing fluid from a high-pressure fluid source to the organ in question, while the second lumen is provided for carrying the rinsing fluid and the solids particles entrained by the rinsing fluid out of the organ.

However, there is no transmission of energy by laser via light guides or a coupling in of this energy provided in this reference, and the means indicated in this disclosure also do not solve the problem of an essentially automatic alignment of two light guides with respect to their optical axes and also with respect to a suction cannula for assembly after cleaning or after exchanging one of the light guides.

OBJECT AND SUMMARY OF THE INVENTION

U.S. Pat. No. 4,785, 805 describes a device for coupling a laser beam coming from its source into a light guide, wherein a collecting lens is arranged in front of the light guide. This device refers to technical means for achieving a centering of the optical axes of the collecting lens and light guide relative to one another as a precondition for coupling in with the least possible losses. However, in this case there is no need, nor are any technical means provided for this purpose, to align the optical axes of the collecting lens and light guide relative to a suction cannula within which the light guide is to extend in a definite position as is the case in a handpiece of the type mentioned above.

To this extent, this device does not satisfy the requirements for use in such a medical handpiece because this medical handpiece requires that the light guide can be removed when worn and that it can be exactly replaced by a new light guide and aligned in a simple manner with the optical axis of the fiber and suction cannula. Also, a handpiece frequently requires disassembly for purposes of cleaning and, for reasons of time and cost, also requires a subsequent simple realignment of the optical axes and suction cannula. This requirement is not met in the device in the above-cited publication.

An adapter for light guide input coupling for a laser device is described in EP 0507991. The adapter contains a sleeve-shaped fitting part for receiving the proximal end of the light guide and is constructed in such a way that blocking and coupling mean are provided in the region of the connection point between the fitting part and a handle, these means enabling the connection of the fitting part and handle only when the light guide is inserted. A light guide for radiating laser energy into biological tissue, for example, which light guide is subject to wear and must therefore be changed frequently and aligned with another light guide and also with a suction cannula in which it extends whenever it is changed, is not provided herein. Consequently, the means disclosed in this reference are not suited to an adequate solution of the above-indicated problems relating to a handpiece.

This relates in an analogous manner to the rinsing catheter according to DE 41 26 886 A1. This rinsing catheter is used to eliminate solids from bodily organs and vessels in humans and animals and is provided with at least two lumens, one of which serves to supply a rinsing fluid from a high-pressure fluid source to the organ in question, while the second lumen is provided for carrying the rinsing fluid and the solids particles entrained by the rinsing fluid out of the organ.

However, there is no transmission of energy by laser via light guides or a coupling in of this energy provided in this reference, and the means indicated in this disclosure also do not solve the problem of an essentially automatic alignment of two light guides with respect to their optical axes and also with respect to a suction cannula for assembly after cleaning or after exchanging one of the light guides.

DESCRIPTION OF THE INVENTION

It is the object of the invention to enable an uncomplicated exchange of the light guide and, further, with little effort on disassembly and assembly to ensure perfect cleaning which satisfies all hygienic requirements.

In a medical handpiece of the type described above, this object is met in that, for purposes of alignment of the optical axis of the light guide with respect to the longitudinal axis of the suction cannula as well as with respect to the optical axis of the radiation-side end of the fiber, at least one adjusting face is allocated in each instance to the light guide, the suction cannula and the fiber so as to be fixed in place, wherein at least one of the adjusting faces assigned to the light guide corresponds with an adjusting face assigned to the suction cannula and with an adjusting face assigned to the fiber, and wherein the light guide is displaceable in the axial direction relative to the base body and the alignment can be produced or canceled depending on the displacement direction.

This construction offers the substantial advantage that the light guide used for radiating laser energy into the tissue is separate from the optical fiber by which the laser radiation is guided from the laser source to the handpiece and can be removed from the handpiece with little effort and exchanged for an unused light guide. The removal of the light guide from the base body of the handpiece is made possible by displacing in the axial direction opposite to the radiation direction of the laser radiation. Conversely, the insertion of the new light guide can be carried out by inserting and pushing forward in the axial direction into the base body of the handpiece, wherein an automatic alignment of the light guide is carried out inside the suction cannula through which the biological tissue which is comminuted by the effect of the laser energy is sucked off from the treatment site. The alignment of the optical fiber is effected relative to the base body of the handpiece and accordingly also relative to the light guide at the same time, while the optical end of the fiber is pushed into the handpiece and centered.

To this extent, means for alignment of the optical axis of the light guide with respect to the longitudinal axis of the suction cannula as well as with respect to the optical axis of the radiation-side end of the fiber are provided in a medical handpiece which has a suction cannula for the comminuted biological tissue in which the light guide extends also. The light guide is also displaceable in the axial direction relative to the suction cannula and the alignment is produced or canceled with the displacement.

It is accordingly ensured with little manual effort that after assembly or after exchanging a used light guide, the light guide will occupy the position provided within the handpiece, and accordingly also within the suction cannula, necessary for the success of the medical treatment. With respect to the cross section of the suction cannula, which is preferably round, the light guide which is also constructed with a round cross section can be arranged centrically. However, an advantageous alternative consists in arranging the light guide so as to be offset with respect to the center of the suction cannula, so that there remains a larger cross-sectional area through which the particles resulting during treatment can be sucked off.

For purposes of alignment, adjusting faces are allocated to the base body and to the light guide, wherein alignment is achieved when these adjusting faces contact directly. Alternatively, these adjusting faces can be constructed as circular-cylindrical faces which form a sliding fit and which are accordingly displaceable relative to one another in the axial direction, or the adjusting faces can be formed as circular-conical faces with an automatically centering slope. One of the surfaces, either the cylindrical surface or the circular-conical surface, is formed as an inner surface while the opposite surface is formed as the outer surface. Further, each centering surface has a circular cross section. The freedom of movement in the axial direction is limited by stops. In this respect, it can be provided that a mechanical spring or a body of elastic material is arranged between the stops, wherein a pretensioning force is generated by the displacement in the axial direction and the pretensioning force can be increased or reduced by the extent of displacement in the axial direction. Further, sealing elements can be provided between the adjoining portions of the stop faces.

The invention is explained more fully in the following with reference to an embodiment example.

DETAILED DESCRIPTION OF THE DRAWING

Figure 1:
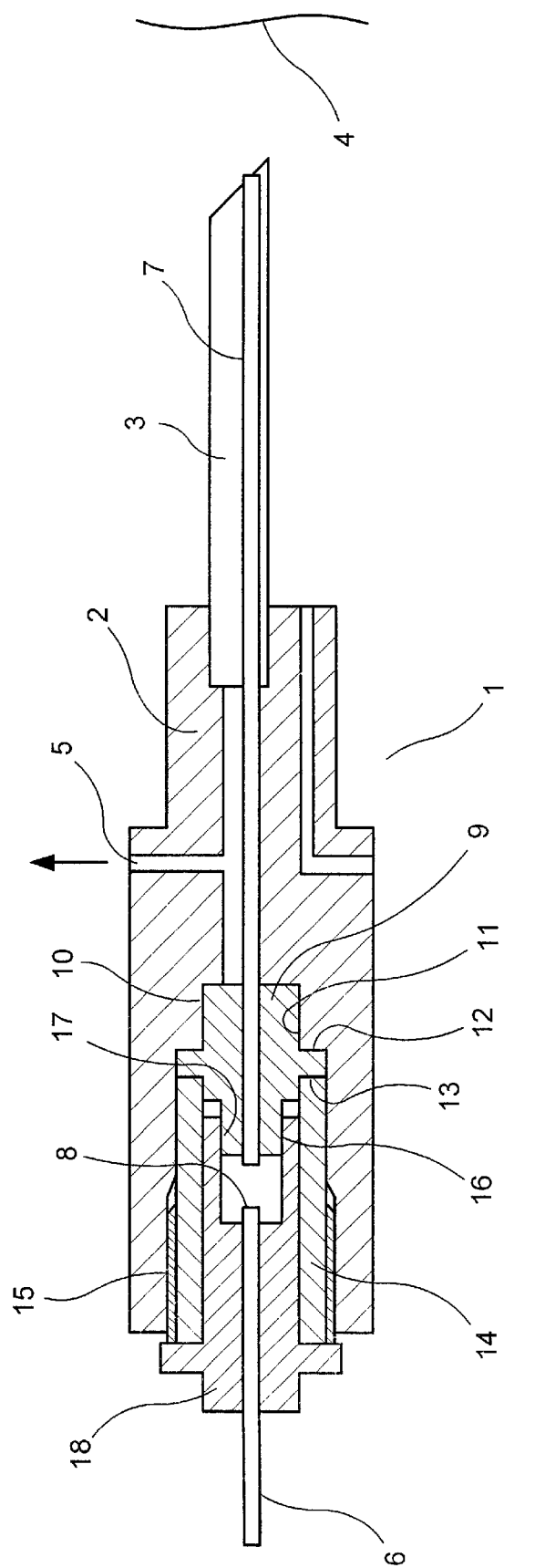
FIG. 1 shows a schematic drawing of the handpiece according to the invention in cross section.

FIG. 1 shows a handpiece 1 for transmitting energy from an IR laser beam into biological tissue, the biological tissue being ablated in this way. A suction cannula 3 through which the biological tissue that is comminuted by the effect of energy is sucked out of the treatment site 4 is fixedly connected with the base body 2. The suction is carried out through the suction cannula 3 and through the suction duct 5 which is incorporated in the base body 2.

An optical fiber 6 is provided for conducting the IR laser radiation, and a light guide 7 made of quartz or sapphire is arranged inside of the suction cannula 3.

In order to ensure reliable functioning of the medical handpiece 1, it is necessary to bring the light guide 7 into a defined position relative to the base body 2 and relative to the suction cannula 3 fastened to the base body 2 and to hold it securely in this position at least during the treatment. Further, it is required that the optical axis of the light guide 7 and the optical axis of the optical fiber 6 are adjusted relative to one another in such a way that radiation energy is coupled out of the optical fiber 6 into the light guide 7 with as little loss as possible.

Based on the object of the invention, which consists in satisfying the requirements mentioned above and, further, in enabling an uncomplicated exchange of the relatively quickly wearing light guide 7 and also a perfect cleaning which satisfies all hygienic requirements, means according to the invention are provided for aligning the optical axis of the light guide 7 relative to the longitudinal axis of the suction cannula 3 and also means are provided for aligning the optical axis of the light guide 7 with respect to the optical axis of the radiation-side end 8 of the optical fiber 6.

To ensure that the light guide 7 can be removed in a simple and uncomplicated manner from the base body 2 and exchanged for an unused one, the means for aligning the optical axis of the light guide 7 are constructed in such a way that the light guide 7 is movable in the axial direction relative to the base body 2 and relative to the suction cannula 3, wherein the alignment of the light guide 7 with respect to the suction cannula 3 is performed along with this movement in the direction of radiation, and this alignment is canceled during a movement in the opposite direction, i.e., opposite to the radiation direction of the laser beam.

In order to achieve this, an adjusting face 10 is assigned to the light guide 7 via a first adjusting piece 9 which, in this case, is fixedly connected with the light guide 7 in a frictional and/or positive engagement. The first adjusting face 10 is formed as a cylindrical outer surface area at the upper surface of adjusting piece 9. For example, the cylindrical axis is aligned parallel with or centric to the optical axis of the light guide 7.

A second adjusting face 11 which is constructed as an inner cylindrical surface and which corresponds to the adjusting face 10 is provided at the base body 2. The two adjusting faces 10 and 11 of adjusting piece 9 together form a sliding fit, so that they are displaceable relative to one another in the axial direction.

As an alternative to the circular-cylindrical adjusting faces 10 and 11, these adjusting faces can be formed as circular-conical faces. The direction of taper of the two circular-conical faces should be identical with the direction of laser radiation, so that the adjusting piece 9 at which the circular-conical face which is formed as an outer surface is located in this case can be removed from the second adjusting face 11 or from the aligned position and from the base body 2 by moving in the axial direction opposite to the laser radiation.

On the other hand, when the light guide 7, with the adjusting piece 9, is inserted in the direction of the optical axis, the two circular-conical faces are automatically centered relative to one another. This also applies in an analogous manner to the construction of the first or second adjusting faces 10 and 11 as cylindrical outer surfaces. In this case, a displacement (limited with respect to displacement distance) of the light guide 7, including the adjusting piece 9, in the axial direction is even possible without the alignment of the light guide 7 relative to the suction cannula 3 being canceled at the same time.

In order to prevent an unintentional displacement of the light guide 7 together with the adjusting piece 9 during the medical treatment, stop faces 12 and 13 are provided, the adjusting piece 9 being enclosed therebetween so as to be fixed with respect to movement (in the axial direction). The stop faces 12 and 13 are arranged at different bodies which can be attached to one another but which are freely movable when disconnected. Accordingly, stop face 12 is formed at the base body 2, while stop face 13 is provided at a bushing 14.

As is shown by way of example in FIG. 1, the bushing 14 can be connected with the base body 2 via a thread 15. By a screwing-in movement of the bushing 14 in the direction of the IR laser radiation until contacting the stop faces 12 and 13 at the adjusting piece 9, the adjusting piece 9 is clamped in the axal direction, so that a change in its position in the axial direction is prevented during use of the medical handpiece 1. On the other hand, if the bushing 14 is loosened by turning in the opposite direction and is removed from the base body 2, the adjusting piece 9 with the light guide 7 is freely movable in the axial direction opposite to the radiation direction and can easily be removed from the base body 2 and replaced with a new adjusting piece 9 with light guide 7 fastened thereto.

In order to realize the alignment of the optical axis of the fiber 6 relative to the optical axis of the light guide 7 in a simple manner, the adjusting piece 9 is outfitted with a third adjusting face 16. The adjusting face 16 is likewise formed as an outer surface of a circular cylinder. It corresponds with a forth adjusting face 17 which is arranged at second adjusting piece 18. The second adjusting piece 18 is connected in a mechanically fixed manner with the radiation-side end 8 of the optical fiber 6. The bushing 14 has a center recess through which the second adjusting piece 18 is inserted until the two adjusting faces 17 and 18 contact one another and an alignment of the optical axis of the fiber 6 relative to the optical axis of the light guide 7 is carried out.

As an alternative to the construction as circular-cylindrical faces, shown herein, the fourth adjusting face 17 and the second adjusting piece 18 can also be circular-conical; however, the taper direction of these two conical surfaces should be carried out opposite to the direction of the IR laser radiation. In this way, it is easily possible when the adjusting piece 18 is moved opposite to the direction of IR laser radiation to cancel the alignment of the two optical axes of the light guide 7 and fiber 6 or to produce this alignment in that the second adjusting piece 18 is inserted into the recess of the bushing 14 in the direction of laser radiation until the centering or alignment of the two optical axes of the fiber 6 and light guide 7 results when the adjusting face 17 and the second adjusting piece 18, which are conical in this instance, slide one over the other.

The handpiece according to the invention enables a quick disassembly of the individual component groups and parts for the purpose of exchanging the light guide 7, wherein the exchange can be used for replacing worn light guides 7 as well as for exchanging light guides 7 with different lengths projecting out of the suction cannula 3 or terminating inside of the suction cannula 3. Moreover, a very quick disassembly is possible for the purpose of clinical cleaning.

As an alternative to the construction of the invention, shown herein, with clamped first adjusting piece 9 which is fixed with respect to movement in the axial direction and accordingly with light guides 7 which are fixed against movement in the axial direction, it can be provided that a mechanical spring or an elastic body is provided between the stop face 11 at the bushing 14 and the corresponding stop face at the first adjusting piece 9 and holds the first adjusting piece 9 against the base body 2 under elastic pretensioning. When a force is applied manually to the light guide 7 in the direction opposite to that of the laser radiation, a change in position of the light guide 7 with the first adjusting piece 9 is possible to a defined extent in the axial direction. Only the pretensioning force of the spring or of the elastic body must be overcome by the acting force.

This offers the advantageous possibility that the distances between the end of the suction cannula 3, the radiation-side end of the light guide 7 and the treatment site 4 can be varied.

What is claimed is:

1. A medical handpiece for transmitting energy from a laser beam into biological tissue comprising:

an optical fiber for conveying the laser radiation;

a light guide for radiating the laser energy into the tissue; and a suction cannula for the biological tissue that is comminuted by the action of the energy and in which the light guide extends;

said optical fiber, light guide and suction cannula being provided in a base body;

for purposes of alignment of the optical axis of the light guide with respect to the longitudinal axis of the suction cannula as well as with respect to the optical axis of the radiation-side end of the fiber, at least one adjusting face being allocated in each instance to the light guide, the suction cannula and the fiber so as to be fixed in place; at least one of the adjusting faces assigned to the light guide corresponding with an adjusting face assigned to the suction cannula and with an adjusting face assigned to the fiber, and said light guide being displaceable in the axial direction relative to the suction cannula; and wherein the alignment can be produced or canceled depending on the displacement direction; and wherein an adjusting face is assigned to the light guide via an adjusting piece, which is fixedly connected with the light guide, stops provided for limiting axial displacement of the light guide and the stops are formed as stop faces vertical to the radiation direction, and at least one stop face is fixed with respect to the light guide and one stop face is fixed with respect to the suction cannula.

2. The handpiece according to claim 1, wherein an adjusting face assigned to the light guide and the adjusting face assigned to the base body or to the suction cannula are constructed as circular-cylindrical faces.

3. The handpiece according to claim 1, wherein the cylindrical surface assigned to the light guide is formed as an outer surface at an adjusting piece and the cylindrical surface assigned to the suction cannula being formed as an inner surface, and both cylindrical surfaces form a sliding fit, so that they are displaceable relative to one another in the axial direction.

4. The handpiece according to claim 1, wherein stops are provided for preventing the axial displacement of the light guide, wherein stop faces of the light guide are enclosed so as to be immovable in the axial direction between stop faces of the suction cannula and another part connected with the handpiece.

5. The handpiece according to claim 1, wherein stops are provided for limiting axial displacement, wherein stop faces of the light guide are enclosed with restricted freedom of movement in the axial direction between stop faces of the suction cannula and another part connected with the handpiece.

6. The handpiece according to claim 1, wherein a mechanical spring or an elastic body is provided between stop faces of the light guide and stop faces of the suction cannula, so that an axial displacement of the light guide is possible by increasing the spring pretensioning force or by deformation of the elastic body.

7. The handpiece according to claim 1, wherein the stop faces between which the stop faces of the light guide are enclosed so as to be immovable or with restricted freedom of movement in the axial direction are formed at different parts of the handpiece which are freely movable relative to one another.

8. The handpiece according to claim 1, wherein the adjusting face assigned to the light guide and the adjusting face assigned to the fiber are constructed as circular-cylindrical surfaces or as circular-conical surfaces with automatic centering properties, wherein the cylinder axes or cone axes extend parallel to the optical axis of the light guide or extend parallel to the optical axis of the fiber.

9. The handpiece according to claim 1, wherein means are provided for the frictional engagement or positive engagement of the light guide with the radiation-side end of the fiber with the optical axes of the light guide and fiber aligned relative to one another.

10. The handpiece according to claim 1, wherein the radiation-side end of the fiber is movable together with the light guide.

11. The handpiece according to claim 1, wherein sealing elements are provided between adjoining portions of the stop faces.

12. The handpiece according to claim 1, wherein the adjusting face assigned to the light guide and the adjusting face assigned to the base body or to the suction cannula are formed as circular-conical surfaces with an automatic centering property.

13. The handpiece according to claim 12, wherein the circular-conical surface assigned to the light guide is formed as an outer surface at an adjusting piece and the circular-conical surface assigned to the suction cannula is formed as an inner surface, and both circular-conical surfaces make contact precisely in the aligned position of the optical axis of the light guide.

14. The handpiece according to claim 13, wherein the direction of taper of the two circular-conical surfaces is identical to the direction of the laser radiation, so that the outer surface can be disengaged from the inner surface through movement in the axial direction, but opposite to the direction of the laser radiation.

15. A medical handpiece for transmitting energy from a laser beam into biological tissue comprising:

an optical fiber for conveying the laser radiation;

a light guide separated from said optical fiber for radiating the laser energy into the tissue; and a suction cannula for the biological tissue that is comminuted by the action of the energy and in which the light guide extends;

said optical fiber, light guide and suction cannula being provided in a base body;

for purposes of automatic alignment of the optical axis of the light guide with respect to the longitudinal axis of the suction cannula as well as with respect to the optical axis of the radiation-side end of the fiber, at least one adjusting face being allocated in each instance to the light guide, the suction cannula and the fiber so as to be fixed in place; at least one of the adjusting faces assigned to the light guide corresponding with an adjusting face assigned to the suction cannula and with an adjusting face assigned to the fiber, and said light guide being displaceable in the axial direction relative to the suction cannula; and wherein the alignment can be produced or canceled depending on the displacement direction; and wherein the adjusting face assigned to the light guide and the adjusting face assigned to the base body or to the suction cannula are formed as circular-conical surfaces with an automatic centering property;

wherein the circular-conical surface assigned to the light guide is formed as an outer surface at an adjusting piece and the circular-conical surface assigned to the suction cannula is formed as an inner surface, and both circular-conical surfaces make contact precisely in the aligned position of the optical axis of the light guide.

* * * * *